US00PP35862P3

(12) United States Plant Patent
Olesen

(10) Patent No.: US PP35,862 P3
(45) Date of Patent: Jun. 11, 2024

(54) MINIATURE ROSE PLANT NAMED 'Poulpah 118'

(50) Latin Name: *Rosa hybrida*
Varietal Denomination: Poulpah118

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,488

(22) Filed: Sep. 8, 2023

(65) Prior Publication Data

US 2024/0107922 P1 Mar. 28, 2024

(30) Foreign Application Priority Data

Sep. 30, 2022 (QZ) ..... PBR 2022/2165

(51) Int. Cl.
*A01H 5/02* (2018.01)
*A01H 6/74* (2018.01)

(52) U.S. Cl.
USPC ..... Plt./128

(58) Field of Classification Search
USPC ..... Plt./101, 123, 128
See application file for complete search history.

*Primary Examiner* — Susan McCormick Ewoldt

(57) ABSTRACT

A new garden rose plant of the miniature class which has abundant, light pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah118'.

This application claims priority to Plant Breeder's Rights Application Number 2022/2165, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah118', originated as a single seedling from the stated cross.

The new variety may be distinguished from its male pollen parent and female seed parent primarily by the following characteristics. The male pollen parent plant has light red flowers while the new variety has light pink flowers. The female seed parent plant has strong perfume, while 'Poulpah118' has little or no flower scent.

The objective of the hybridization of this rose variety was to create a new and distinct variety with unique qualities, such as:

1. Uniform and abundant light pink flowers;
2. Vigorous, but compact growth when propagated on its own roots;
3. Exceptional disease resistance.

This combination of qualities is not present in previously available commercial cultivars of this type, known to the inventor, and distinguish 'Poulpah118' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah118' was selected in the spring of 2016 by the inventor as a single plant from the progeny of the aforementioned hybridization.

Asexual reproduction of 'Poulpah118' by rooted cuttings was first done by Mogens N. Olesen in the nursery in Fredensborg, Denmark in July, 2016. This initial and other subsequent asexual propagations conducted in controlled environments have demonstrated that the characteristics of 'Poulpah118' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah118'.

Specifically illustrated in FIG. 1 of the drawings are an open flower viewed from above, a flower bud upon opening, petals detached, a flower bud, and sepals detached revealing reproductive flower parts.

Figure 1:
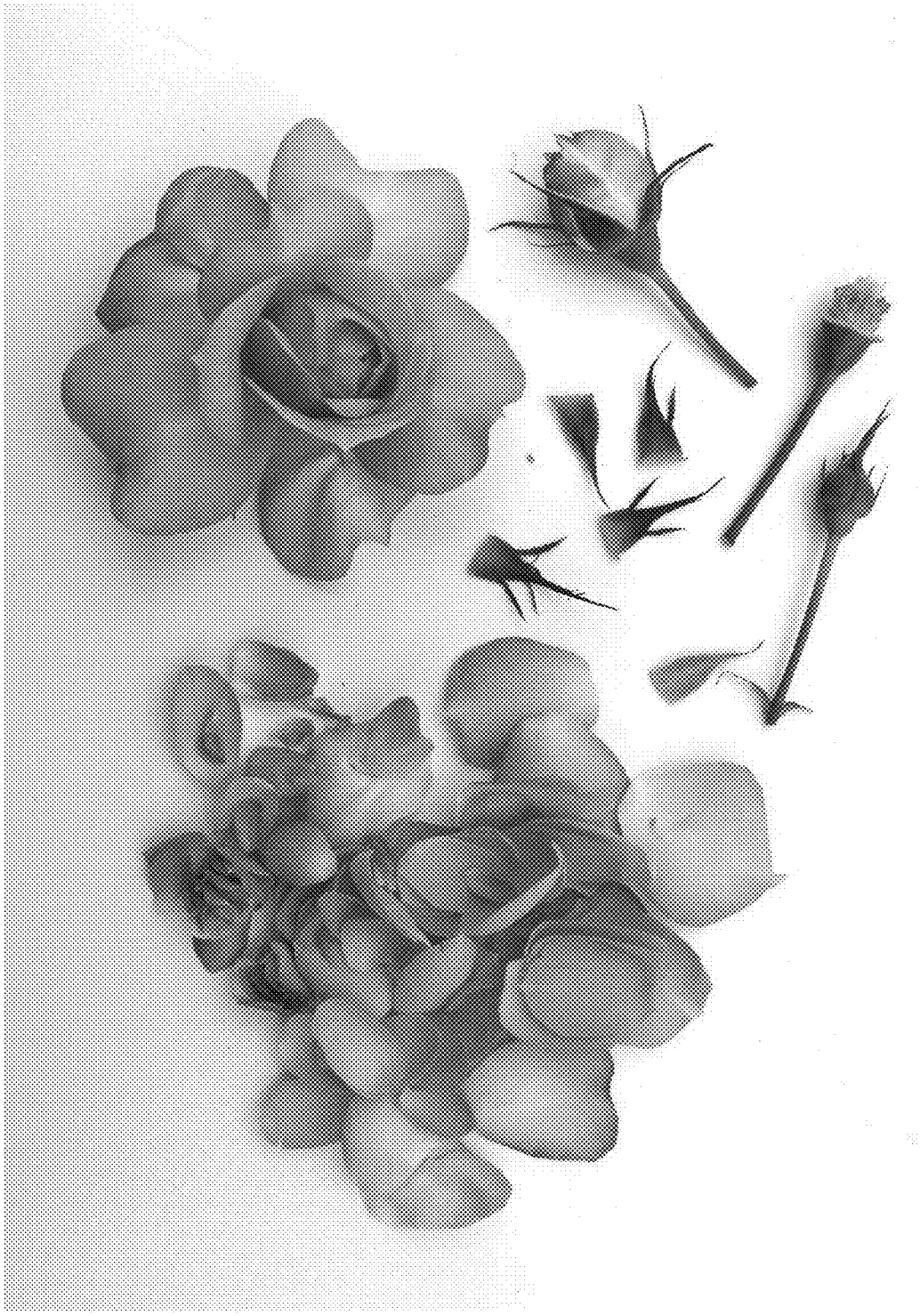
Figure 2:
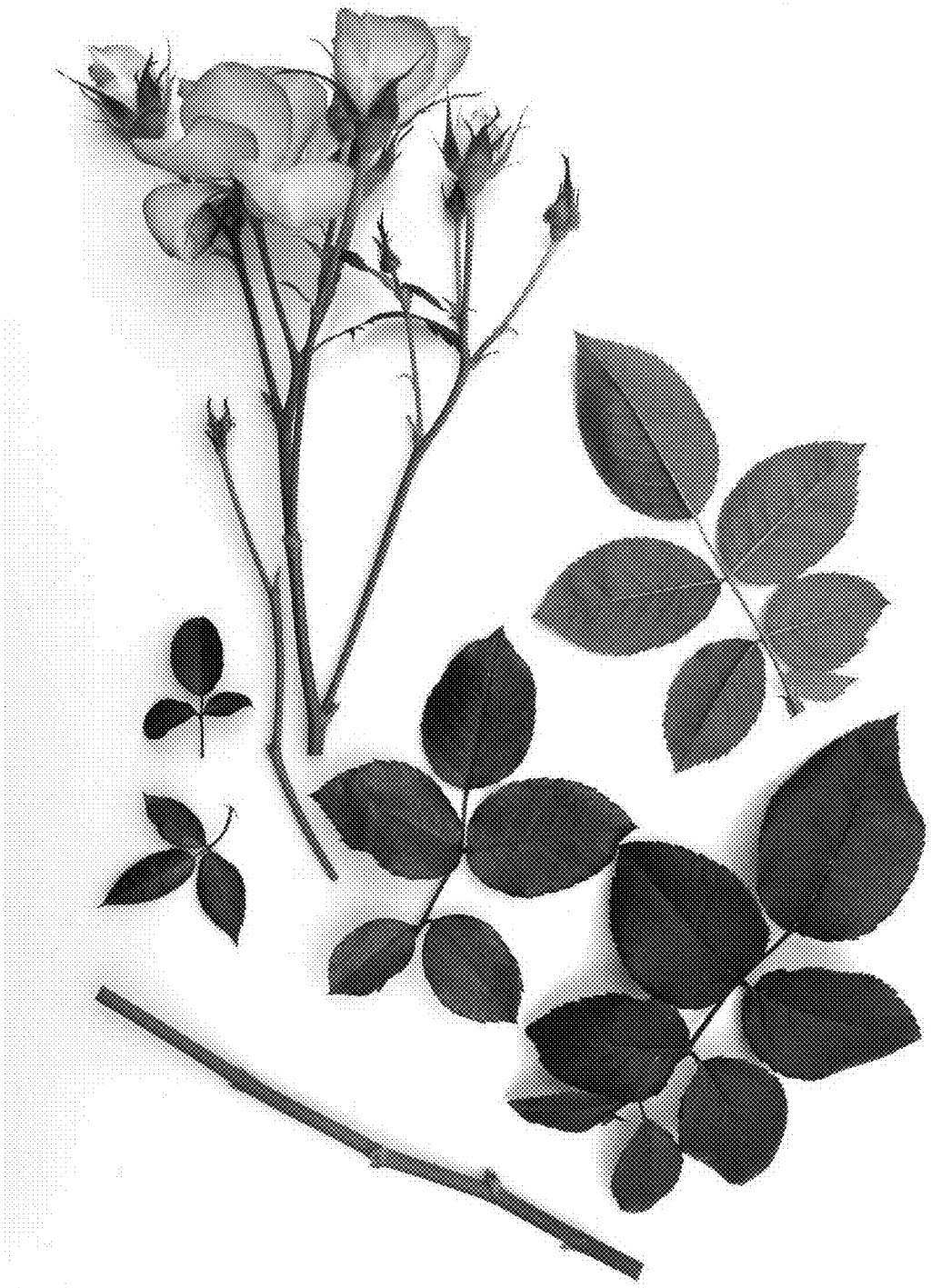

Specifically illustrated in FIG. 2 of the drawings are a cluster of flowers on a branch, juvenile leaflet growth exhibiting strong anthocyanin, mature leaves, and a bare stem exhibiting prickles.

Plants shown are 5 months of age.

DETAILED DESCRIPTION OF THE VARIETY

The following is a description of 'Poulpah118', as observed in its growth in an indoor glasshouse nursery in Odense Denmark. Observed plants are 5 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpah086', U.S. Plant Pat. No. 29,701 are compared to the claimed plant. While 'Poulpah118' has 95 flower petals, 'Poulpah086' has 40 flower petals. The claimed plant has a flower diameter of 75 mm while 'Poulpah086' has a flower diameter of 55 mm. Open flowers of 'Poulpah118' are generally Red Group 55B in color while 'Poulpah086' has a general tonality of Red-Purple Group 62A.

FLOWER AND FLOWER BUD

Blooming habit: Continuous.

Flower bud:

*Size.*—Upon opening, 18 mm in length from base of receptacle to end of bud. Bud diameter is 12 mm.

*Bud form.*—Globose.

*Bud color.*—As sepals divide petals are White Group 155A and Red Group 53C.

*Sepal inner surface.*—Color: Yellow-Green Group 146D. Surface: Lightly pubescent.

*Sepal outer surface.*—Color: Yellow-Green Group 144A. At the apex Greyed-Purple Group 187C. Texture: Rough with stipitate glands.

*Sepal shape.*—Apex: Cirrhose. Base: Flat at union with receptacle.

*Sepal margin.*—Margins have strong foliaceous appendages on three of the five sepals.

*Sepal size.*—About 27 mm long, 9 mm wide.

*Receptacle.*—Texture: Smooth. Size: 9 mm in height, 10 mm wide. Color: Yellow-Green Group 144A. Shape: Campanulate.

*Pedicel.*—Surface: Smooth. Length: 36 mm. Diameter: 2 mm on average. Color: Yellow-Green Group 144A. Strength: Strong.

*Peduncle.*—Length: 25 to 30 mm. Diameter: About 3. mm. Color: Yellow-Green Group 144A. Texture: Smooth.

*Flower bud development.*—Flower buds are borne singly or in clusters of 7 to 9 flower buds per stem.

Flower bloom:

*Fragrance.*—Light floral.

*Duration.*—The blooms have a duration on the plant of approximately 21 days. Petals fall cleanly away from plant after flowers have fully matured.

*Size.*—Flower diameter is 75 mm when open. Flower depth is 35 mm.

*Flower shape.*—High centered, very double, with a high pointed center which is tightly closed.

*Shape of flower, side view.*—The upper and lower portion are flat.

Petalage: Under normal conditions, flowers have about 95 petals.

General tonality of flower: Open flowers are Red Group 55B.

Petal color:

*Upon opening, outer petals.*—Upper surface: Red Group 55B splashed with Red Group 55D. Lower surface: At the basal zone White Group N155B. Middle zone to marginal zone Red-Purple Group N57C. Marginal intonations of Red-Purple Group N57A.

*Upon opening, inner petals.*—Upper surface: Red Group 49A. At the basal zone Yellow Group 2C. Lower surface: Red Group 49B with shades of Red-Purple Group 62A.

*Basal petal spots, upon opening.*—Upper surface: Yellow Group 2D. Lower surface: Yellow Group 2D.

*After opening, outer petals.*—Upper surface: Red Group 55C with White 155B streaks. Basal zone Green White Group 157A. Lower surface: Red-Purple Group 62B, with marginal intonations of Red-Purple Group 57B. Central bar White 155A.

*After opening, inner petals.*—Upper surface: Red Group 49A with basal zone Yellow Group 2D. Lower surface: Red Group 56A with intonations of Red-Purple Group 62A at the margins. Basal zone Yellow Group 2D.

Petals:

*Petal Reflex.*—Slightly reflexed.

*Margin.*—Entire and uniform with a single point at the center of the apex. No undulations.

*Shape.*—Broad and elliptic: Apex shape: Rounded. Base shape: Acute or somewhat obtuse.

*Size.*—44 mm (l)×41 mm (w).

*Texture.*—Smooth.

*Thickness.*—Average.

Petaloids:

*Size.*—10 mm (l) by 6 mm (w).

*Quantity.*—About 30.

*Shape.*—Elliptical with an acute base and rounded apex.

*Color.*—The upper surface is Red Group 43C. The lower surface is Red Group 51B. Yellow Group 2C at the point of attachment on both sides.

Reproductive flower parts:

*Pollen.*—None observed.

*Anthers.*—Size: 2 mm in length. Color: Yellow Group 13A. Quantity: 30 on average.

*Filaments.*—Color: Yellow Group 6C. Length: 4 mm.

*Pistils.*—Length: 10 mm. Quantity: 23 on average.

*Stigmas.*—Color: Yellow Group 4D.

*Styles.*—Color: Yellow Group 4D.

*Location of stigmas.*—Superior in location relative to the length of the filaments and the height of the anthers.

*Hips.*—None Observed.

PLANT

Plant growth: Upright. Plants are 53 cm in height, and 32 cm wide.

Stems:

*Color of juvenile growth.*—Yellow-Green Group 144B.

*Color of mature growth.*—Yellow-Green Group 146A.

*Length.*—Canes are about 36 cm from the base of the plant to the flowering portion.

*Diameter.*—About 4 mm.

*Internodes.*—On mature canes about 33 mm between nodes.

*Surface texture.*—Young wood: Smooth. Older wood: Smooth.

Long prickles: None observed.

Plant foliage:

*Compound leaf.*—140 to 170 mm (l)×120 to 125 (w).

*Quantity.*—3 or 2 leaves per 10 cm of stem on average.

*Leaf bearing angle to the stem.*—45 degrees.

*Color of juvenile foliage.*—Upper side: Greyed-Purple Group 187A with light intonations of Yellow-Green Group 146B. Lower side: Greyed-Purple Group 187A with light intonations of Yellow-Green Group 146B.

*Color of mature foliage.*—Upper side: Yellow-Green Group 147A. Lower side: Yellow-Green Group 147B.

Plant leaves and leaflets:

*Stipules.*—Size: 11 mm long, mm wide. Quantity: 2 per compound leaf. Shape: Linear, slightly broad based with outward extending apices. Margins: Finely serrated. Color: Yellow-Green Group 144A.

*Petiole.*—Length: About 12 mm. Diameter: 2 mm. Upper surface color: Yellow-Green Group 144A with anthocyaning Greyed-Red Group 180A. Lower surface color: Yellow-Green Group 144A.

*Rachis.*—Length: About 50 mm. Upper surface color: Greyed-Purple Group 187D. Lower surface color: Yellow-Green Group 144A.

*Leaflet.*—Quantity: Normally 5 to 7 leaflets. Margins: Serrated. Size: Terminal leaflets are about 65 to 70 mm long, 40 to 50 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah118' substantially as described and illustrated herein.

* * * * *